(12) United States Patent
Barth et al.

(10) Patent No.: US 7,462,631 B2
(45) Date of Patent: Dec. 9, 2008

(54) THIOPHENE-2-CARBOXAMIDE DERIVATIVES, PREPARATION AND THERAPEUTIC APPLICATION THEREOF

(75) Inventors: Francis Barth, Saint Georges D'Orques (FR); Jean-Philippe Ducoux, Combaillaux (FR); Murielle Rinaldi-Carmona, Saint Georges D'Orques (FR); Christian Congy, Saint Gely du Fesc (FR)

(73) Assignee: Sanofi-Aventis, Paris (FR)

( * ) Notice: Subject to any disclaimer, the term of this patent is extended or adjusted under 35 U.S.C. 154(b) by 102 days.

(21) Appl. No.: 11/400,702

(22) Filed: Apr. 7, 2006

(65) Prior Publication Data

US 2006/0264470 A1    Nov. 23, 2006

Related U.S. Application Data

(63) Continuation of application No. PCT/FR2004/002546, filed on Oct. 8, 2004.

(30) Foreign Application Priority Data

Oct. 10, 2003   (FR) .................... 03 11861

(51) Int. Cl.
*A61K 31/453*   (2006.01)
*A61K 31/405*   (2006.01)
*A61K 31/381*   (2006.01)
*C07D 333/24*   (2006.01)

(52) U.S. Cl. ............... 514/326; 514/414; 514/444; 514/448; 546/207; 548/465; 549/59; 549/72

(58) Field of Classification Search ............ 514/326, 514/414, 444, 448; 546/207; 548/465; 549/59, 549/72
See application file for complete search history.

(56) References Cited

FOREIGN PATENT DOCUMENTS

| | | |
|---|---|---|
| EP | 0728755 | 8/1996 |
| WO | WO 91/19708 | 12/1991 |
| WO | WO 91/19708 A1 * | 12/1991 |
| WO | WO 95/00501 | 1/1995 |
| WO | WO 03/037886 | 5/2003 |

OTHER PUBLICATIONS

Shvedov, V.I., et. al., Synthesis and Biological Activity of 5-Aryithiphene-2-Carboxylic Acid Derivatives, Khimicko-Farmatsevticheskii Zhurnal, vol. 12, No. 11, (1978) pp. 53-56.
Tsuji, K., et. al., Studies on Anti-Inflammatory Agents. VI. 1) Synthesis and Pharmacological Properties of 2,3-Diarylthiophenes, Chem Pharm. Bull., vol. 46(2), pp. 279-286 (1998).

* cited by examiner

*Primary Examiner*—Rei-Tsang Shiao
*Assistant Examiner*—Joseph R Kosack
(74) *Attorney, Agent, or Firm*—Balaram Gupta

(57) ABSTRACT

The invention discloses and claims a compound of formula (I):

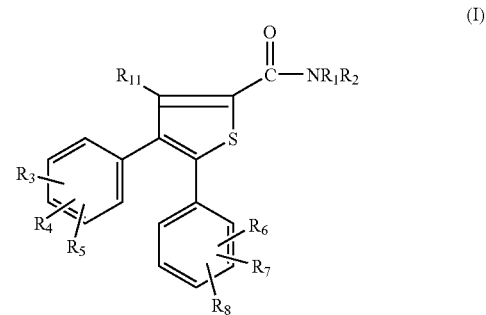

Wherein $R_1$, $R_2$, $R_3$, $R_4$, $R_5$, $R_6$, $R_7$, $R_8$ and $R_{11}$ are as defined herein. Further embodiments of the invention include a method of preparation of a compound of formula (I), its pharmaceutical composition and a method of treatment of a disease using a compound of formula (I).

20 Claims, No Drawings

THIOPHENE-2-CARBOXAMIDE DERIVATIVES, PREPARATION AND THERAPEUTIC APPLICATION THEREOF

CROSS REFERENCE TO RELATED APPLICATIONS

This application is a continuation of International application No. PCT/FR2004/002,546, filed Oct. 8, 2004, which is incorporated herein by reference in its entirety; which claims the benefit of priority of French Patent Application No. 03/11,861, filed Oct. 10, 2003.

BACKGROUND OF THE INVENTION

1. Field of the Invention

The subject of the present invention is thiophene-2-carboxamide derivatives, their preparation and their therapeutic application.

2. Description of the Art

Diphenylpyrazole derivatives with affinity for the $CB_1$ cannabinoid receptors have been described in particular in U.S. Pat. No. 5,624,941, EP 0 576 357, EP 0 656 354 and EP 1 150 961.

5,6-Diphenyl-2-pyrazinecarboxamide derivatives are described in International Patent Application WO 03/051850 as $CB_1$ receptor antagonists.

1,2-Diphenyl-4-imidazolecarboxamide derivatives are described in International Patent Application WO 03/027076 as $CB_1$ receptor agonists, partial agonists or antagonists.

4,5-Diarylthiophene derivatives having analgesic properties are described in International Application WO 91/19708.

All of the references described herein are incorporated herein by reference in their entirety.

SUMMARY OF THE INVENTION

Novel thiophene-2-carboxamide derivatives have now been found which possess antagonist properties for the $CB_1$ cannabinoid receptors. Thus, the subject of the present invention is compounds corresponding to formula (I):

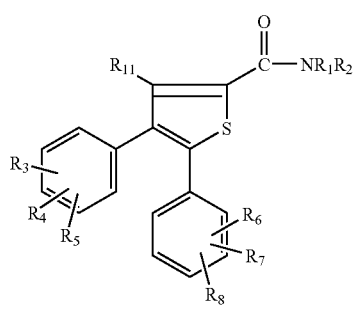

in which:
$R_1$ represents hydrogen or a $(C_1-C_4)$alkyl;
$R_2$ represents:
- a $(C_4-C_{10})$alkyl group;
- a nonaromatic $C_3-C_{12}$ carbocyclic radical which is unsubstituted or substituted once or several times with a $(C_1-C_4)$alkyl, $(C_1-C_4)$alkoxy or hydroxyl group;
- a 1,2,3,4-tetrahydronaphthyl- 1 or -2;
- a saturated monooxygen- or monosulfur-containing heterocyclic radical of 5 to 7 atoms which is unsubstituted or substituted once or several times with a $(C_1-C_4)$alkyl group;
- a saturated mononitrogen-containing heterocyclic radical of 5 to 7 atoms, the nitrogen atom being substituted with a $(C_1-C_4)$alkyl, phenyl, benzyl, $(C_1-C_4)$alkoxycarbonyl or $(C_1-C_4)$alkanoyl group;
- a $(C_1-C_3)$alkylene group carrying a nonaromatic $C_3-C_{10}$ carbocyclic radical which is unsubstituted or substituted once or several times with a $(C_1-C_4)$alkyl group;
- a phenylalkylene group in which the alkylene is $(C_1-C_3)$, which is unsubstituted or substituted on the alkylene with one or more methyl groups, and/or which is substituted on the phenyl with one or more identical or different substituents chosen from a halogen atom or a $(C_1-C_4)$alkyl, trifluoromethyl, $(C_1-C_4)$alkoxy or trifluoromethoxy group;
- a methylene which is substituted with a benzothienyl, benzofuryl, thienyl or furyl radical, said radicals being unsubstituted or substituted with one or more $(C_1-C_4)$alkyl groups;
- an $NR_9R_{10}$ group;

or $R_1$ and $R_2$ together with the nitrogen atom to which they are attached constitute either a piperazin-1-yl or 1,4-diazepan-1-yl radical which is substituted at the 4-position with a phenyl or benzyl group, or a piperidin-1-yl or pyrrolidin-1-yl radical which is mono- or gem-disubstituted with a phenyl, benzyl, $(C_1-C_4)$alkyl, hydroxyl, $(C_1-C_4)$alkoxy, cyano, $(C_1-C_3)$alkanoyl, $(C_1-C_4)$alkoxycarbonylamino or $(C_1-C_3)$alkanoylamino group; the phenyl or benzyl groups being unsubstituted or substituted once or several times with a halogen atom and/or a $(C_1-C_4)$alkyl and/or $(C_1-C_4)$alkoxy and/or trifluoromethyl group;

$R_3, R_4, R_5, R_6, R_7, R_8$ each represent independently of each other a hydrogen or halogen atom, or a $(C_1-C_6)$alkyl, $(C_1-C_6)$alkoxy, trifluoromethyl or $S(O)_n$Alk group;

$R_9$ represents a hydrogen atom or a methyl group;

$R_{10}$ represents a $(C_3-C_6)$alkyl, phenyl or $C_3-C_{10}$ cycloalkyl group, said phenyl and cycloalkyl groups being unsubstituted or substituted with one or more halogen atoms and/or $(C_1-C_4)$alkyl groups;

or $R_9$ and $R_{10}$ together with the nitrogen atom to which they are attached constitute a saturated or unsaturated heterocyclic radical of 5 to 11 atoms, bridged or otherwise, comprising or otherwise a spiro carbon and containing or otherwise a second heteroatom chosen from O or N, said radical being unsubstituted or substituted with a hydroxyl or phenyl group or once or several times with a $(C_1-C_4)$alkyl and/or $(C_1-C_4)$alkoxy group;

$R_{11}$ represents a hydrogen atom or a $(C_1-C_4)$alkyl or $(C_3-C_7)$cycloalkyl group;

n represents 0, 1 or 2;

Alk represents a $(C_1-C_4)$alkyl group;

and their salts, their solvates and their hydrates.

The compounds of formula (I) may contain one or more asymmetric carbon atoms. They can therefore exist in the form of enantiomers or of diastereoisomers. These enantiomers, diastereoisomers and mixtures thereof, including the racemic mixtures, form part of the invention.

The compounds of formula (I) can exist in the form of bases or of addition salts with acids. These salts are advantageously prepared with pharmaceutically acceptable salts but the salts of other acids which are useful, for example, for the purification or isolation of the compounds of formula (I) also form part of the invention.

DETAILED DESCRIPTION OF THE INVENTION

The expression alkyl group is understood to mean a linear or branched radical such as in particular: methyl, ethyl, propyl, isopropyl, butyl, isobutyl, tert-butyl, n-pentyl, isopentyl, n-hexyl, isohexyl, the methyl group being preferred for a ($C_1$-$C_4$)alkyl, the tert-butyl, 2-methylbut-2-yl or 3,3-dimethylbut-2-yl groups being preferred for a ($C_3$-$C_6$)alkyl.

The expression alkylene group is understood to mean a linear or branched divalent radical, methylene, 1-methylmethylene and ethylene being preferred.

The expression alkoxy group is understood to mean a linear or branched radical, the methoxy group being preferred.

The expression halogen atom is understood to mean a fluorine, chlorine, bromine or iodine atom; fluorine, chlorine or bromine atoms being preferred.

The nonaromatic $C_3$-$C_{12}$ carbocyclic radicals comprise fused or bridged mono- or polycyclic radicals. The monocyclic radicals include cycloalkyls, for example cyclopropyl, cyclobutyl, cyclopentyl, cyclohexyl, cycloheptyl, cyclooctyl; cyclohexyl and cyclopentyl being preferred. The fused, bridged or spiro di- or tricyclic radicals include for example the norbornyl, bornyl, isobornyl, noradamantyl, adamantyl, spiro[5.5]undecanyl, bicyclo[2.2.1]heptyl, bicyclo-[3.2.1]octyl and bicyclo[3.1.1]heptyl radicals.

The expression saturated or unsaturated heterocyclic radical of 5 to 11 atoms, containing or otherwise a second heteroatom such as O or N, is understood to mean radicals such as morpholin-4-yl, piperidin-1-yl, piperazin-1-yl, pyrrolidin-1-yl, octahydrocyclopenta[c]pyrrol-2-yl, hexahydrocyclopenta[c]pyrrol-2-yl, 8-azabicyclo[3.2.1]octanyl and 8-aza[4.5]decanyl radicals, the piperidin-1-yl and morpholin-4-yl radicals being preferred.

The expression saturated mononitrogen-containing heterocyclic radical of 5 to 7 atoms is understood to mean a radical such as piperidin-4-yl or pyrrolidin-3-yl, the piperidin-4-yl radical being preferred.

The expression saturated monooxygen-containing heterocyclic radical of 5 to 7 atoms is understood to mean a radical such as tetrahydrofuranyl, tetrahydro-2H-pyranyl or oxepanyl; tetrahydrofuranyl being preferred.

According to the present invention, there can be distinguished the compounds of formula (I) in which:
$R_1$ represents hydrogen or a ($C_1$-$C_4$)alkyl;
$R_2$ represents:
  a ($C_4$-$C_{10}$)alkyl group;
  a nonaromatic $C_3$-$C_{12}$ carbocyclic radical which is unsubstituted or substituted once or several times with a ($C_1$-$C_4$)alkyl group;
  a 1,2,3,4-tetrahydronaphthyl-1 or -2;
  a saturated monooxygen- or monosulfur-containing heterocyclic radical of 5 to 7 atoms which is unsubstituted or substituted once or several times with a ($C_1$-$C_4$)alkyl group;
  a saturated mononitrogen-containing heterocyclic radical of 5 to 7 atoms, the nitrogen atom being substituted with a ($C_1$-$C_4$)alkyl, phenyl, benzyl, ($C_1$-$C_4$)alkoxycarbonyl or ($C_1$-$C_4$)alkanoyl group;
  a ($C_1$-$C_3$)alkylene group carrying a nonaromatic $C_3$-$C_{10}$ carbocyclic radical which is unsubstituted or substituted once or several times with a ($C_1$-$C_4$)alkyl group;
  a phenylalkylene group in which the alkylene is ($C_1$-$C_3$), which is unsubstituted or substituted on the alkylene with one or more methyl groups, and/or which is substituted on the phenyl with one or more identical or different substituents chosen from a halogen atom or a ($C_1$-$C_4$)alkyl, trifluoromethyl, ($C_1$-$C_4$)alkoxy or trifluoromethoxy group;
  a methylene which is substituted with a benzothienyl, benzofuryl, thienyl or furyl radical, said radicals being unsubstituted or substituted with one or more ($C_1$-$C_4$)alkyl groups;
  an $NR_9R_{10}$ group;
  or $R_1$ and $R_2$ together with the nitrogen atom to which they are attached constitute either a piperazin-1-yl or 1,4-diazepan-1-yl radical which is substituted at the 4-position with a phenyl or benzyl group, or a piperidin-1-yl or pyrrolidin-1-yl radical which is mono- or gem-disubstituted with a phenyl, benzyl, ($C_1$-$C_4$)alkyl, hydroxyl, ($C_1$-$C_3$)alkanoyl or ($C_1$-$C_4$)alkoxycarbonylamino group; the phenyl or benzyl groups being unsubstituted or substituted once or several times with a halogen atom and/or a methyl group;
$R_3$, $R_4$, $R_5$, $R_6$, $R_7$, $R_8$ each represent independently of each other a hydrogen or halogen atom, or a ($C_1$-$C_6$)alkyl, ($C_1$-$C_6$)alkoxy, trifluoromethyl or $S(O)_n$Alk group;
$R_9$ represents a hydrogen atom or a methyl group;
$R_{10}$ represents a ($C_3$-$C_6$)alkyl, phenyl or $C_3$-$C_{10}$ cycloalkyl group, said phenyl and cycloalkyl groups being unsubstituted or substituted with one or more halogen atoms and/or ($C_1$-$C_4$)alkyl groups or with a halogen atom;
or $R_9$ and $R_{10}$ together with the nitrogen atom to which they are attached constitute a saturated or unsaturated heterocyclic radical of 5 to 11 atoms, bridged or otherwise, comprising or otherwise a spiro carbon and containing or otherwise a second heteroatom chosen from O or N, said radical being unsubstituted or substituted with a hydroxyl or phenyl group or, once or several times, with a ($C_1$-$C_4$)alkyl group;
$R_{11}$ represents a hydrogen atom;
n represents 0, 1 or 2;
Alk represents a ($C_1$-$C_4$)alkyl group;

and their salts, their solvates and their hydrates.

According to the present invention, there can be distinguished the compounds of formula (I), in which:
$R_1$ represents hydrogen or a ($C_1$-$C_4$)alkyl;
$R_2$ represents a ($C_7$-$C_{10}$)alkyl group;

the other substituents being as defined for (I); and their salts, their solvates and their hydrates.

According to the present invention, there can also be distinguished the compounds of formula (I), in which:
$R_{11}$ represents a ($C_1$-$C_4$)alkyl or ($C_3$-$C_7$)cycloalkyl group;

the other substituents being as defined above for (I); and their salts, their solvates and their hydrates.

According to the present invention, there are preferred the compounds of formula (I), in which:
$R_1$ and $R_2$ together with the nitrogen atom to which they are attached constitute a piperidin-1-yl radical which is gem-disubstituted with a benzyl or phenyl group which is unsubstituted or substituted with a halogen atom and with a ($C_1$-$C_3$)alkanoyl or cyano group;
or $R_1$ represents hydrogen;
and/or $R_2$ represents a group $NR_9R_{10}$ in which $R_9$ and $R_{10}$ together with the nitrogen atom to which they are attached constitute a saturated heterocyclic radical of 5 to 11 carbon atoms, which is unsubstituted or substituted once or several times with a ($C_1$-$C_4$)alkyl;

and/or $R_2$ represents a nonaromatic $C_3$-$C_{10}$ carbocyclic radical which is unsubstituted or substituted once or several times with a $(C_1$-$C_4)$alkyl group;

and/or $R_2$ represents a benzyl group which is substituted on the phenyl with one or more identical or different substituents chosen from a halogen atom or a $(C_1$-$C_4)$alkyl, trifluoromethyl, $(C_1$-$C_4)$alkoxy or trifluoromethoxy group;

and/or $R_3$, $R_4$, $R_5$, $R_6$, $R_7$, $R_8$ each represent independently of each other a hydrogen or halogen atom, preferably $R_3$ is 4-chloro or 4-bromo, and $R_6$ and $R_7$ represent 2,4-dichloro, $R_4$, $R_5$ and $R_8$ representing a hydrogen atom;

and their salts, their solvates and their hydrates.

The present invention relates in particular to the following compounds:

4-(4-chlorophenyl)-5-(2,4-dichlorophenyl)-3-methyl-N-piperidin-1-ylthiophene-2-carboxamide;

2-{[4-(4-chlorophenyl)-5-(2,4-dichlorophenyl)-3-methyl-2-thienyl]carbonyl}octahydrocyclopenta[c]pyrrole;

1-(1-{[5-(4-chlorophenyl)-4-(2,4-dichlorophenyl)-2-thienyl]carbonyl}-4-phenylpiperidin-4-yl)ethanone;

1-(1-{[4-(4-chlorophenyl)-5-(2,4-dichlorophenyl)-2-thienyl]carbonyl}-4-phenylpiperidin-4-yl)-ethanone.

The subject of the present invention is also a method for preparing the compounds according to the invention.

This method is characterized in that the acid of formula (II) or a functional derivative of this acid of formula:

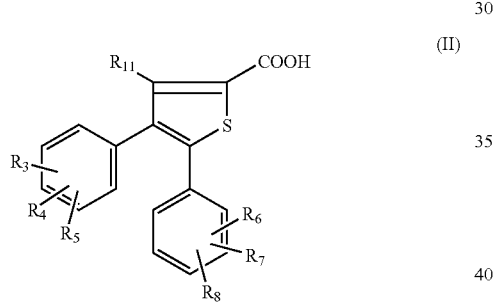

(II)

in which $R_3$, $R_4$, $R_5$, $R_6$, $R_7$, $R_8$ and $R_{11}$ are as defined for (I), is treated with an amine of formula $HNR_1R_2$ (III) in which $R_1$ and $R_2$ are as defined for (I). Optionally, the compound thus obtained is converted to one of its salts or solvates.

As a functional derivative of the acid (II), it is possible to use the acid chloride, the anhydride, a mixed anhydride, a $C_1$-$C_4$ alkyl ester in which the alkyl is straight or branched, an activated ester, for example p-nitrophenyl ester, or the free acid opportunely activated, for example, with N,N-di-cyclohexylcarbodiimide or with benzotriazol-1-yloxo-tris(dimethylamino)phosphonium hexafluorophosphate (BOP) or benzotriazol-1-yloxotris(pyrrolidino)-phosphonium hexafluorophosphate (PyBOP).

Thus, in the method according to the invention, it is possible to react the chloride of pyrazole-3-carboxylic acid, obtained by reacting thionyl chloride with the acid of formula (II), with an amine $HNR_1R_2$, in an inert solvent, such as a chlorinated solvent (dichloromethane, dichloroethane, chloroform for example), an ether (tetrahydrofuran, dioxane for example), or an amide (N,N-dimethylformamide for example) under an inert atmosphere, at a temperature of between 0° C. and room temperature, in the presence of a tertiary amine such as triethylamine, N-methyl-morpholine or pyridine.

A variant consists in preparing the mixed anhydride of the acid of formula (II) by reacting ethyl chloroformate with the acid of formula (II), in the presence of a base such as triethylamine, and in reacting it with an amine $HNR_1R_2$, in a solvent such as dichloromethane, under an inert atmosphere, at room temperature, in the presence of a base such as triethylamine.

When $R_{11}$ represents a hydrogen atom, the compounds of formula (II) may be prepared according to F. Vögtle et al., Chem., Ber., 1983, 116, 3112-3124, which is incorporated herein by reference in its entirety, and reported in the Scheme 1 below:

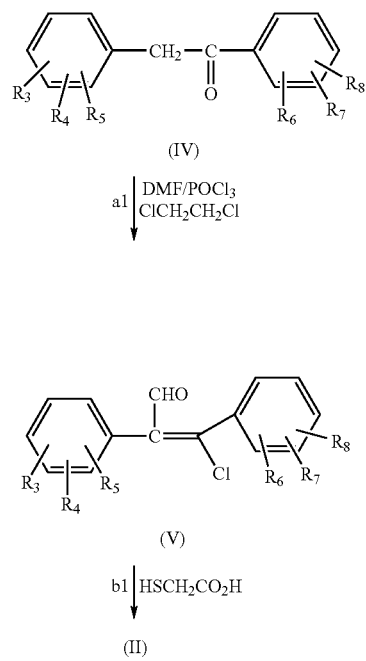

The preparation of the compound of formula (IV) is carried out according to the method described in International Patent Application WO 03/007887, which is incorporated herein by reference in its entirety.

In step b1), the cyclization with mercapto-acetic acid is carried out in the presence of triethylamine.

When $R_{11}$ is other than hydrogen, the compound of formula (V) is prepared according to Scheme 1 above and then the procedure is carried out as described below in Scheme 2:

SCHEME 2

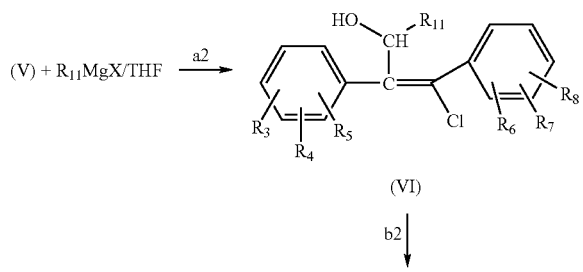

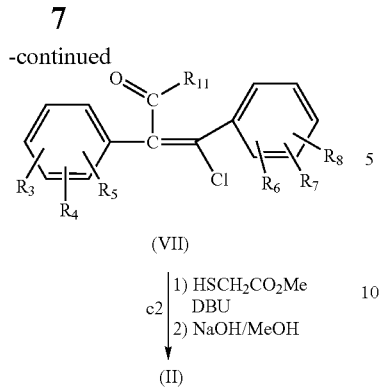

$$\text{(VII)} \xrightarrow[\substack{\text{2) NaOH/MeOH}}]{\substack{\text{1) HSCH}_2\text{CO}_2\text{Me} \\ \text{DBU}}} \text{(II)}$$

In step a2), the compound of formula (V) is treated with an organomagnesium compound of formula $R_{11}MgX$ in which $R_{11}$ is as defined for (I) and X represents a halogen atom, preferably bromine.

The compound thus obtained of formula (VI) is treated in step b2) with an oxidizing agent such as $MnO_2$, pyridinium dichromate (PDC), pyridinium chloro-chromate or the Dess-Martin reagent described in Dess D. B., Martin J. C., J. Am. Chem. Soc., 1991, 113, 7277-7287, which is incorporated herein by reference in its entirety. In step c2), the cyclization with the mercaptoacetic acid ester is carried out in the presence of DBU and then the ester obtained is hydrolyzed with sodium hydroxide to form the acid of formula (II).

The following examples describe the preparation of some compounds in accordance with the invention. These examples are not limiting and merely illustrate the present invention. The exemplified compound numbers refer to those given in the tables below, which illustrate the chemical structures and the physical properties of a few compounds according to the invention.

In the examples, the following abbreviations are used:
m.p.: melting point
AcOEt: ethyl acetate
BOP: benzotriazol-1-yloxytris(dimethylamino)-phosphonium hexafluorophosphate
RT: room temperature
TBTU: O-benzotriazol-1-yl-N,N,N',N'-tetramethyluronium tetrafluoroborate
DCM: dichloromethane
DBU: 1,8-diazabicyclo[5.4.0]undec-7-ene.

The nuclear magnetic resonance spectra are recorded at 200 MHz in DMSO-$d_6$. For the interpretation of the spectra, the following abbreviations are used: s: singlet, d: doublet, t: triplet, m: unresolved complex, mt: multiplet, bs: broad singlet.

The compounds according to the invention are analyzed by LC/UV/MS (liquid chromatography/UV detection/mass spectrometry) coupling. The molecular peak (MH$^+$) and the retention time (t) in minutes are measured.

There is used an Xterra Waters® MS C18 column, marketed by Waters, of 2.1×30 mm, 3.5 μm, at room temperature, flow rate 1 ml/minute.

The eluent is made up as follows:
solvent A: 0.025% of trifluoroacetic acid (TFA) in water
solvent B: 0.025% of TFA in acetonitrile.

Gradient: the percentage of solvent B varies from 0 to 100% over 2 minutes with a plateau at 100% of B for 1 minute.

The UV detection is carried out between 210 nm and 400 nm and the mass detection in chemical ionization mode at atmospheric pressure.

EXAMPLE 1

Compound 27

4-(4-Chlorophenyl)-5-(2,4-dichlorophenyl)-N-piperidin-1-ylthiophene-2-carboxamide A) 3-Chloro-2-(4-chlorophenyl)-3-(2,4-dichlorophenyl)-acrylaldehyde 7 ml of POCl$_3$ are added dropwise to a solution of 6.6 ml of DMF in 4 ml of dichloroethane, cooled to −5° C., under nitrogen, and then the temperature is allowed to rise and 7 g of 2-(4-chlorophenyl)-1-(2,4-dichlorophenyl)ethanone are added. The reaction medium is heated at 50° C. for 16 hours and then the mixture is poured into 100 ml of ice-cold water. The medium is extracted with DCM and then the organic phase is washed with a saturated NaHCO$_3$ solution, water, and then an NaCl solution. 1.45 g of the expected compound are obtained, which compound crystallizes from isopropyl ether, m.p.=128° C.

B) 4-(4-Chlorophenyl)-5-(2,4-dichlorophenyl) thiophene-2-carboxylic acid 1.40 g of the compound in the preceding step are placed in 1 ml of pyridine cooled on an ice bath, and then 0.28 ml of mercaptoacetic acid and 1.24 ml of triethylamine are added dropwise. The medium is allowed to return to RT, kept stirring for 30 minutes and then heated at 70° C. for 3 hours. The medium is cooled to RT and then diluted with 2 ml of EtOH, a solution of 0.57 g of KOH in 4 ml of EtOH is added and the medium is heated for 3 hours under reflux. The reaction medium is poured into 100 ml of an ice-cold solution of HCl at 10%. The precipitate formed is filtered and then washed with water and dried. 1.20 g of the expected compound are obtained.

C) 4-(4-Chlorophenyl)-5-(2,4-dichlorophenyl)-N-piperidin-1-ylthiophene-2-carboxamide 0.60 g of the compound obtained in the preceding step is placed in 15 ml of DCM and 0.54 ml of triethylamine is added followed by 0.18 ml of 1-amino-piperidine and, at 0° C., 0.80 g of BOP. The medium is kept stirring at RT for 3 hours and then the reaction medium is poured into ice-cold water. The medium is extracted with DCM, washed with water and then with a saturated NaCl solution. The medium is chromatographed on silica, eluting with an AcOEt/toluene (10/90; v/v) mixture, and then the expected product is crystallized from a DCM/isopropyl ether mixture. 90 mg are obtained, m.p.=232° C.

EXAMPLE 2

Compound 33

4-(4-Chlorophenyl)-5-(2,4-dichlorophenyl)-3-methyl-N-piperidin-1-ylthiophene-2-carboxamide A) 4-Chloro-3-(4-chlorophenyl)-4-(2,4-dichlorophenyl)-but-3-en-2-ol 4 g of the compound obtained in step A of Example 1 are placed in 40 ml of anhydrous THF, and then 12.72 ml of methylmagnesium bromide in a normal solution in THF at −20° C. are added and the temperature is allowed to rise to RT.

NH4Cl is added and the medium is extracted with ethyl acetate. The organic phase is dried over MgSO4 and evaporated off. The product obtained is chromatographed on silica, eluting with a heptane/AcOEt mixture. 1.3 g of the expected compound are obtained.

B) 4-Chloro-3-(4-chlorophenyl)-4-(2,4-dichlorophenyl)-but-3-en-2-one 1 g of the compound obtained in the preceding step is placed in 30 ml of DCM and 2.6 g of 4 Å molecular sieve are added, followed by 2.5 g of pyridinium dichromate. After 24 hours at RT, the medium is filtered on Celite® and the solvent is evaporated to dryness. The product is chromatographed on silica, eluting with a heptane/AcOEt mixture. 1 g of the expected product is obtained $MH^+$=359, $t^-$=11.81 minutes.

C) Methyl 4-(4-chlorophenyl)-5-(2,4-dichlorophenyl)-3-methylthiophene-2-carboxylate 1 g of the compound obtained in the preceding step is placed in 25 ml of acetonitrile and 0.37 ml of methyl thioglycolate is added, followed by 0.34 ml of DBU and the medium is kept stirring for 24 hours at RT. The solvent is evaporated to dryness and the medium is extracted with ethyl acetate, washed with NH4Cl and then with a 0.5N HCl solution. The organic phase is dried over MgSO4 and evaporated off. The product is chromatographed on silica, eluting with a heptane/AcOEt mixture. 0.5 g of the expected product is obtained.

D) 4-(4-Chlorophenyl)-5-(2,4-dichlorophenyl)-3-methylthiophene-2-carboxylic acid 0.5 g of the compound obtained in the preceding step is placed in 20 ml of MeOH and 0.0486 g of NaOH is added. The medium is kept stirring at room temperature for 24 hours and the reaction medium is then evaporated off. The organic impurities are extracted with ether and the aqueous phase is acidified to pH=1. The acid is extracted with ethyl acetate and the organic phase is dried and then evaporated off. 260 mg of the expected product are obtained.

E) 4-(4-Chlorophenyl)-5-(2,4-dichlorophenyl)-3-methyl-N-piperidin-1-ylthiophene-2-carboxamide 0.25 g of the compound in the preceding step is placed in 15 ml of DCM and 0.22 ml of triethylamine is added, followed by 0.063 g of N-aminopiperidine and then 0.222 g of TBTU and the medium is kept stirring for 24 hours at RT. The reaction medium is evaporated to dryness, water is added and the medium is extracted with AcOEt, and washed with a 0.5N sodium hydroxide solution. The organic phase is dried and evaporated to dryness. The product crystallizes from ether. 0.2 g of the expected product is obtained.

$MH^+$=481, t=12.10.

The tables which follow illustrate the chemical structures and the physical properties of a few compounds according to the invention. In this table: Me, Et, tBu represent methyl, ethyl and tert-butyl groups, respectively.

TABLE 1

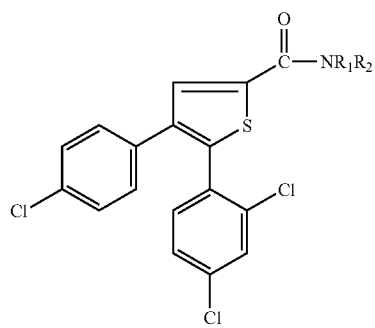

(I)

| Compounds | $R_1$ | $R_2$ | Characterization |
|---|---|---|---|
| 1 | H | —N(Me)₂ | $MH^+$ = 425.55<br>t = 2.31 |
| 2 | H | —CH(CH₃)—C₆H₄—Cl (racemic) | $MH^+$ = 519.96<br>t = 2.35 |
| 3 | H | —N(piperazinyl)—Me | $MH^+$ = 480.62<br>t = 1.92 |
| 4 | H | —N(pyrrolidinyl) | $MH^+$ = 451.39<br>t = 2.32 |
| 5 | H | —NH—C₆H₄—tBu | $MH^+$ = 529.44<br>t = 2.67 |
| 6 | $NR_1R_2$: —N(pyrrolidinyl with NH—COOtBu) (racemic) | | $MH^+$ = 551.67<br>t = 3.29 |
| 7 | H | —CH₂—(furanyl)—Me | $MH^+$ = 476.60<br>t = 3.48 |
| 8 | H | —(CH₂)₂—tBu | $MH^+$ = 466.60<br>t = 3.60 |
| 9 | H | —CH₂—C₆H₄—OCF₃ | $MH^+$ = 556.59<br>t = 3.59 |
| 10 | $NR_1R_2$: —N(homopiperazinyl)—CH₂—C₆H₅ | | $MH^+$ = 555.45<br>t = 2.00 |

TABLE 1-continued

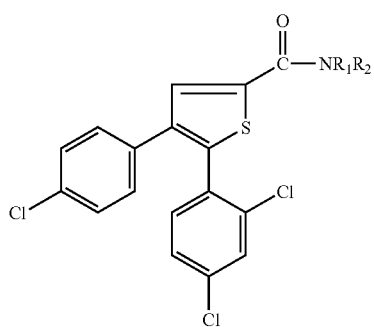

(I)

| Compounds | R₁ | R₂ | Characterization |
|---|---|---|---|
| 11 | H | (+) isopinocampheyl | MH⁺ = 518.43<br>t = 2.82 |
| 12 | H | (structure: bicyclic with Me, Me, H) | MH⁺ = 503.85<br>t = 2.62 |
| 13 | H | —N(piperidine)—OH (N-methyl) | MH⁺ = 481.41<br>t = 2.18 |
| 14 | H | —CH(CH₃)—tBu (R) | MH⁺ = 466.07<br>t = 2.22 |
| 15 | H | —CH₂-(-) cis myrtanyl | MH⁺ = 518.13<br>t = 2.37 |
| 16 | H | 3-methylcyclohexyl, cis, trans mixture | MH⁺ = 478.08<br>t = 2.25 |

TABLE 1-continued

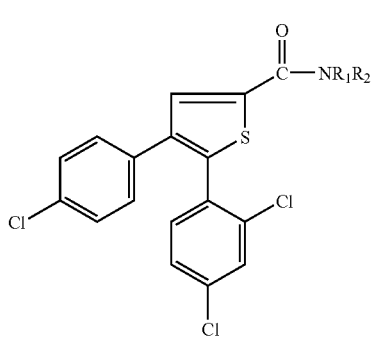

(I)

| Compounds | R₁ | R₂ | Characterization |
|---|---|---|---|
| 17 | H | R (+) bornyl | MH⁺ = 518.10<br>t = 2.35 |
| 18 | H | (R)-1,2,3,4-tetrahydronaphthalen-1-yl | MH⁺ = 512.03<br>t = 2.25 |
| 19 | H | tetrahydrothiophen-2-yl | MH⁺ = 468.00<br>t = 2.11 |
| 20 | H | —(CH₂)—phenyl | MH⁺ = 486.02<br>t = 1.25 |
| 21 | H | n-pentyl | MH⁺ = 452.05<br>t = 2.20 |
| 22 | H | —CH₂—CH₂—(3-chlorophenyl) | MH⁺ = 519.99<br>t = 2.21 |
| 23 | H | 4-methylcyclohexyl, cis, trans mixture | MH⁺ = 478.08<br>t = 2.26 |
| 24 | H | —CH₂—(2-CF₃-phenyl) | MH⁺ = 540.02<br>t = 2.21 |

TABLE 1-continued (I)

| Compounds | R₁ | R₂ | Characterization |
|---|---|---|---|
| 25 | H | 4-methyl-4-tBu-cyclohexyl (cis, trans mixture) | MH⁺ = 520.14 t = 2.42 |
| 26 | H | adamantyl | m.p. = 218° C. |
| 27 | H | piperidin-1-yl | m.p. = 232° C. |

TABLE 2

(I)

| Compounds | R₃, R₄ | R₆, R₇ | R₁₁ | —NR₁R₂ | Characterization |
|---|---|---|---|---|---|
| 29 | 4-Cl | 2,4-diCl | H | —NH-adamantyl | MH⁺ = 516  t = 13.91 |
| 30 | 4-Cl | 2,4-diCl | H | —NH-(N-benzyl-azabicyclo) | MH⁺ = 581  t = 8.32 |
| 31 | 4-Cl | 2,4-diCl | H | —NH—N(4-Me-4-Et-piperidinyl) | MH⁺ = 507  t = 13.63 |

TABLE 2-continued (I)

| Compounds | R₃, R₄ | R₆, R₇ | R₁₁ | —NR₁R₂ | Characterization |
|---|---|---|---|---|---|
| 32 | 4-Cl | 2,4-diCl | H | N-methylpiperidine with 4-phenyl and 4-C(O)Me | MH⁺ = 570<br>t = 12.56 |
| 33 | 4-Cl | 2,4-diCl | Me | —NH—piperidinyl | MH⁺ = 481<br>t = 12.10 |
| 34 | 4-Cl | 2,4-diCl | H | N-methylpiperidine with 4-C(O)Me and 4-CH₂-phenyl | MH⁺ = 582<br>t = 12.15 |
| 35 | 4-Cl | 2,4-diCl | H | N-methylpiperidine with 4-phenyl and 4-CN | MH⁺ = 551<br>t = 12.02 |
| 36 | 4-Cl | 2,4-diCl | Me | N-methylpiperidine with 4-phenyl and 4-C(O)Me | MH⁺ = 582<br>t = 12.70 |
| 37 | 4-Cl | 2,4-diCl | Me | —NH—octahydrocyclopenta[c]pyrrolyl | MH⁺ = 505<br>t = 12.46 |
| 38 | 4-Cl | 2,4-diCl | H | N-methylpiperidine with 4-phenyl and 4-NHC(O)Me | MH⁺ = 583<br>t = 10.80 |
| 39 | 4-Cl | 2,4-diCl | Me | —NH—2-azaspiro[5.5]undecane type | MH⁺ = 533<br>t = 12.97 |

TABLE 2-continued (I)

| Compounds | R₃, R₄ | R₆, R₇ | R₁₁ | —NR₁R₂ | Characterization |
|---|---|---|---|---|---|
| 40 | 4-Cl | 2,4-diCl | H | N-methylpiperidine with OMe and CH₂-phenyl at 4-position | MH⁺ = 570<br>t = 12.52 |
| 41 | 4-Cl | 2,4-diCl | H | N-methylpiperidine with CN and 4-chlorophenyl at 4-position | MH⁺ = 585<br>t = 12.40 |
| 42 | 2,4-diCl | 4-Cl | H | bicyclic amine with gem-dimethyl | MH⁺ = 504<br>t = 12.89 |
| 43 | 2,4-diCl | 4-Cl | H | N-methylpiperidine with CN and 4-chlorophenyl at 4-position | MH⁺ = 596<br>t = 12.48 |
| 44 | 2,4-diCl | 4-Cl | H | N-methylpiperidine with acetyl and phenyl at 4-position | MH⁺ = 568<br>t = 12.64 |
| 45 | 4-Br | 2,4-diCl | H | N-methylpiperidine with acetyl and phenyl at 4-position | MH⁺ = 612<br>t = 11.40 |
| 46 | 4-Br | 2,4-diCl | H | N-methylpiperidine with CN and 4-chlorophenyl at 4-position | MH⁺ = 595<br>t = 12.53 |
| 47 | 4-Br | 2,4-diCl | H | bicyclic amine with gem-dimethyl | MH⁺ = 547<br>t = 13.58 |

TABLE 2-continued

*Formula (I): thiophene core with C(=O)-NR₁R₂ at position 2, R₁₁ at position 3, phenyl (with R₃, R₄) at position 4, phenyl (with R₆, R₇) at position 5.*

| Compounds | R₃, R₄ | R₆, R₇ | R₁₁ | —NR₁R₂ | Characterization |
|---|---|---|---|---|---|
| 48 | 4-Br | 2,4-diCl | Me | —HN—N(octahydropentalenyl) | MH⁺ = 549, t = 12.84 |
| 49 | 4-Br | 2,4-diCl | Me | —NH—N(piperidinyl) | MH⁺ = 523, t = 12.06 |
| 50 | 4-Br | 2,4-diCl | Me | —HN—N(spiro[5.5]) | MH⁺ = 577, t = 13.77 |
| 51 | 2,4-diCl | 4-Cl | Me | —HN—N(octahydropentalenyl) | MH⁺ = 505, t = 12.82 |
| 52 | 2,4-diCl | 4-Cl | Me | —HN—N(piperidinyl) | MH⁺ = 479, t = 12.22 |
| 53 | 2,4-diCl | 4-Cl | Me | —HN—N(spiro[5.5]) | MH⁺ = 533, t = 13.25 |

The compounds of formula (I) possess a good in vitro ($IC_{50} \leq 5 \times 10^{-7}$M) for the $CB_1$ cannabinoid receptors, under the experimental conditions described by M. Rinaldi-Carmona et al. (FEBS Letters, 1994, 350, 240-244).

The antagonist nature of the compounds of formula (I) has been demonstrated by the results obtained in adenylate cyclase inhibition models as described in M. Rinaldi-Carmona et al., J. Pharmacol. Exp. Ther., 1996, 278, 871-878 and M. Bouaboula et al., J. Biol. Chem., 1997, 272, 22330-22339.

The compounds according to the invention have been tested in vivo (binding ex vivo) in mice after intravenous and/or oral administration, according to the experimental conditions described by Rinaldi-Carmona et al. (J. Pharmacol. Exp., 1998, 284, 644-650).

The toxicity of the compounds of formula (I) is compatible with their use as a medicament.

According to another of its aspects, the present invention relates to the use of a compound of formula (I), or of one of its pharmaceutically acceptable salts, solvates or hydrates, for the preparation of medicaments intended for treating or preventing diseases involving the $CB_1$ cannabinoid receptors.

For example and without limitation, the compounds of formula (I) are useful as psychotropic medicaments, in particular for the treatment of psychiatric disorders including anxiety, depression, mood disorders, insomnia, delirium disorders, obsessive disorders, psychoses in general, schizophrenia, and for the treatment of disorders linked to the use of psychotropic substances, in particular in the case of a substance abuse and/or of dependence on a substance, including alcohol dependence and nicotine dependence.

The compounds of formula (I) according to the invention may be used as medicaments for the treatment of migraine, stress, diseases of psychosomatic origin, panic attacks, epileptic attacks, motion disorders, in particular dyskinesia or Parkinson's disease, tremors and dystonia.

The compounds of formula (I) according to the invention can also be used as medicaments in the treatment of memory disorders, cognitive disorders, in particular in the treatment of senile dementia, Alzheimer's disease, and in the treatment of attention or vigilance disorders. Furthermore, the compounds of formula (I) may be useful as neuroprotectants, in the treatment of ischemia, cranial traumas and the treatment of neurodegenerative diseases: including chorea, Huntington's chorea, Tourette's syndrome.

The compounds of formula (I) according to the invention can be used as medicaments in the treatment of pain: neuropathic pain, acute peripheral pain, chronic pain of inflammatory origin.

The compounds of formula (I) according to the invention may be used as medicaments in the treatment of appetite disorders, craving disorders (for sugars, carbohydrates, drugs, alcohol or any appetizing substance) and/or eating disorders, in particular as anorexiants or for the treatment of obesity or of bulimia and for the treatment of type II diabetes or non-insulin-dependent diabetes and for the treatment of dyslipidemia, of metabolic syndrome. Furthermore, the compounds of formula (I) according to the invention may be used as medicaments in the treatment of gastrointestinal disorders, diarrheal disorders, ulcers, emesis, bladder and urinary disorders, disorders of endocrine origin, cardiovascular disorders, hypotension, hemorrhagic shock, septic shock, chronic cirrhosis of the liver, nonalcoholic hepatic steatosis, asthma, Raynaud's syndrome, glaucoma, fertility disorders, inflammatory phenomena, immune system diseases, in particular autoimmune and neuroinflammatory diseases such as rheumatoid arthritis, reactive arthritis, diseases causing demyelination, multiple sclerosis, infectious and viral diseases such as encephalitis, stroke and as medicaments for anticancer chemotherapy, for the treatment of Guillain-Barré syndrome and for the treatment of osteoporosis.

According to the present invention, the compounds of formula (I) are particularly useful for the treatment of psychotic disorders, in particular schizophrenia; attention deficit hyperactivity disorders (ADHD) in hyperkinetic children (MBD); for the treatment of appetite disorders and obesity; for the treatment of memory and cognitive disorders; for the treatment of alcohol dependence, nicotine dependence, that is to say for withdrawal from alcohol and for smoking cessation; and for the treatment of dyslipidemia, and of metabolic syndrome.

According to one of its aspects, the present invention relates to the use of a compound of formula (I), of its pharmaceutically acceptable salts and of their solvates or hydrates, for the treatment of the disorders and diseases indicated above.

The compound according to the invention is generally administered in dosage unit form.

Said dosage units are preferably formulated in pharmaceutical compositions in which the active ingredient is mixed with a pharmaceutical excipient.

Thus according to another of its aspects, the present invention relates to pharmaceutical compositions containing, as active ingredient, a compound of formula (I), one of its pharmaceutically acceptable salts or one of their solvates.

The compound of formula (I) above and its pharmaceutically acceptable salts or solvates may be used in daily doses of 0.01 to 100 mg per kg of body weight of the mammal to be treated, preferably in daily doses of 0.02 to 50 mg/kg. In human beings, the dose can vary preferably from 0.05 to 4000 mg per day, more particularly from 0.1 to 1000 mg per day according to the age of the subject to be treated or the type of treatment, namely prophylactic or curative. Although these dosages are examples of average situations, there may be particular cases when higher or lower dosages are appropriate, such dosages also belong to the invention. According to customary practice, the dosage appropriate for each patient is determined by the doctor according to the mode of administration, the age, the weight and the response of said patient.

In the pharmaceutical compositions of the present invention for oral, sublingual, inhaled, subcutaneous, intramuscular, intravenous, transdermal, local or rectal administration, the active ingredient may be administered in unit form for administration, mixed with conventional pharmaceutical carriers, to animals and to humans. The appropriate unit forms for administration comprise the forms by the oral route such as tablets, gelatin capsules, powders, granules and oral solutions or suspensions, the forms for sublingual or buccal administration, aerosols, the forms for topical administration, implants, the forms for subcutaneous, intramuscular, intravenous, intranasal or intraocular administration and the forms for rectal administration.

In the pharmaceutical compositions of the present invention, the active ingredient is generally formulated in dosage units containing from 0.05 to 1000 mg, advantageously from 0.1 to 500 mg, preferably from 1 to 200 mg of said active ingredient per dosage unit for daily administrations.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:

1. A compound of the formula (I):

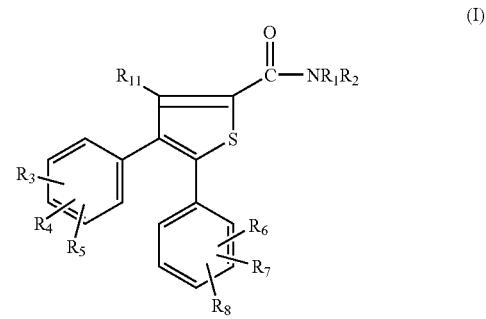

in which:

$R_1$ represents hydrogen or a $(C_1-C_4)$alkyl;

$R_2$ represents:

a nonaromatic $C_3-C_{12}$ carbocyclic radical which is unsubstituted or substituted once or several times with a $(C_1-C_4)$alkyl, $(C_1-C_4)$alkoxy or hydroxyl group;

a 1,2,3,4-tetrahydronaphthyl-1 or -2;

a saturated monooxygen- or monosulfur-containing heterocyclic radical of 5 to 7 atoms which is unsubstituted or substituted once or several times with a $(C_1-C_4)$alkyl group;

a saturated mononitrogen-containing hetero cyclic radical of 5 to 7 atoms, the nitrogen atom being substituted with a $(C_1-C_4)$alkyl, phenyl, benzyl, $(C_1-C_4)$alkoxycarbonyl or $(C_1-C_4)$alkanoyl group;

a $(C_1-C_3)$alkylene group carrying a nonaromatic $C_3-C_{10}$ carbocyclic radical which is unsubstituted or substituted once or several times with a $(C_1-C_4)$alkyl group;

a phenylalkylene group in which the alkylene is $(C_1-C_3)$, which is unsubstituted or substituted on the alkylene with one or more methyl groups, and in which the phenyl is unsubstituted or substituted with one or more identical or different substituents chosen from a halogen atom or a $(C_1-C_4)$alkyl, trifluoromethyl, $(C_1-C_4)$alkoxy or trifluoromethoxy group;

a methylene which is substituted with a benzothienyl, benzofuryl, thienyl or furyl radical, said radicals being unsubstituted or substituted with one or more $(C_1-C_4)$ alkyl groups;

an $NR_9R_{10}$ group;

or $R_1$ and $R_2$ together with the nitrogen atom to which they are attached constitute either a piperazin-1-yl or 1,4-diazepan-1-yl radical which is substituted at the 4-position with a phenyl or benzyl group, or a piperidin-1-yl or pyrrolidin-1-yl radical which is mono- or gem-disubstituted with a phenyl, benzyl, $(C_1-C_4)$alkyl, hydroxyl, $(C_1-C_4)$alkoxy, cyano, $(C_1-C_3)$alkanoyl, $(C_1-C_4)$alkoxycarbonylamino or $(C_1-C_3)$alkanoylamino group; the phenyl or benzyl groups being unsubstituted or substituted once or several times with a halogen atom or a $(C_1-C_4)$alkyl or $(C_1-C_4)$alkoxy or trifluoromethyl group;

$R_3, R_4, R_5, R_6, R_7, R_8$ each represent independently of each other a hydrogen or halogen atom, or a $(C_1-C_6)$alkyl, $(C_1-C_6)$alkoxy, trifluoromethyl or $S(O)_n$Alk group;

$R_9$ represents a hydrogen atom or a methyl group;

$R_{10}$ represents a $(C_3-C_6)$alkyl, phenyl or $C_3-C_{10}$ cycloalkyl group, said phenyl and cycloalkyl groups being unsubstituted or substituted with one or more halogen atoms and/or $(C_1-C_4)$alkyl groups;

or $R_9$ and $R_{10}$ together with the nitrogen atom to which they are attached constitute a saturated or unsaturated heterocyclic radical of 5 to 11 atoms, bridged or otherwise, comprising or otherwise a spiro carbon and containing or otherwise a second heteroatom chosen from O or N, said radical being unsubstituted or substituted with a hydroxyl or phenyl group or, once or several times, with a $(C_1-C_4)$alkyl and/or $(C_1-C_4)$alkoxy group;

$R_{11}$ represents a hydrogen atom or a $(C_1-C_4)$alkyl or $(C_3-C_7)$cycloalkyl group;

n represents 0, 1 or 2;

Alk represents a $(C_1-C_4)$alkyl group; and said compound in the form of a base or an addition salt with an acid.

2. The compound as claimed in claim 1 of formula (I), in which:

$R_1$ represents hydrogen or a $(C_1-C_4)$alkyl;

$R_2$ represents:

a nonaromatic $C_3-C_{12}$ carbocyclic radical which is unsubstituted or substituted once or several times with a $(C_1-C_4)$alkyl group;

a 1,2,3,4-tetrahydronaphthyl-1 or -2;

a saturated monooxygen- or monosulfur-containing heterocyclic radical of 5 to 7 atoms which is unsubstituted or substituted once or several times with a $(C_1-C_4)$alkyl group;

a saturated mononitrogen-containing heterocyclic radical of 5 to 7 atoms, the nitrogen atom being substituted with a $(C_1-C_4)$alkyl, phenyl, benzyl, $(C_1-C_4)$alkoxycarbonyl or $(C_1-C_4)$alkanoyl group;

a $(C_1-C_3)$alkylene group carrying a nonaromatic $C_3-C_{10}$ carbocyclic radical which is unsubstituted or substituted once or several times with a $(C_1-C_4)$alkyl group;

a phenylalkylene group in which the alkylene is $(C_1-C_3)$, which is unsubstituted or substituted on the alkylene with one or more methyl groups, and in which the phenyl is unsubstituted or substituted with one or more identical or different substituents chosen from a halogen atom or a $(C_1-C_4)$alkyl, trifluoromethyl, $(C_1-C_4)$alkoxy or trifluoromethoxy group;

a methylene which is substituted with a beuzothienyl, benzofuryl, thienyl or furyl radical, said radicals being unsubstituted or substituted with one or more $(C_1-C_4)$alkyl groups;

an $NR_9R_{10}$ group;

or $R_1$ and $R_2$ together with the nitrogen atom to which they are attached constitute either a piperazin-1-yl or 1,4-diazepan-1-yl radical which is substituted at the 4-position with a phenyl or benzyl group, or a piperidin-1-yl or pyrrolidin-1-yl radical which is mono- or gem-disubstituted with a phenyl, benzyl, $(C_1-C_4)$alkyl, hydroxyl, $(C_1-C_3)$alkanoyl or $(C_1-C_4)$alkoxycarbonylamino group; the phenyl or benzyl groups being unsubstituted or substituted once or several times with a halogen atom and/or a methyl group;

$R_3, R_4, R_5, R_6, R_7, R_8$ each represent independently of each other a hydrogen or halogen atom, or a $(C_1-C_6)$alkyl, $(C_1-C_6)$alkoxy, trifluoromethyl or $S(O)_n$Alk group;

$R_9$ represents a hydrogen atom or a methyl group;

$R_{10}$ represents a $(C_3-C_6)$alkyl, phenyl or $C_3-C_{10}$ cycloalkyl group, said phenyl and cycloalkyl groups being unsubstituted or substituted with one or more halogen atoms or $(C_1-C_4)$alkyl groups;

or $R_9$ and $R_{10}$ together with the nitrogen atom to which they are attached constitute a saturated or unsaturated heterocyclic radical of 5 to 11 atoms, optionally containing bridged or a spiro carbon and optionally containing a second heteroatom chosen from O or N, said radical being unsubstituted or substituted once or several times with a hydroxyl or phenyl group or a $(C_1-C_4)$alkyl group;

$R_{11}$ represents a hydrogen atom;

n represents 0, 1 or 2;

Alk represents a $(C_1-C_4)$alkyl group; and said compound in the form of a base or an addition salt with an acid.

3. The compound as claimed in claim 1 of formula (I), in which $R_{11}$ represents a $(C_1-C_4)$alkyl or $(C_3-C_7)$cycloalkyl group.

4. The compound as claimed in claim 1 of formula (I), in which:

$R_1$ and $R_2$ together with the nitrogen atom to which they are attached constitute a piperidin-1-yl radical which is gem-disubstituted with a benzyl or phenyl group which is unsubstituted or substituted with a halogen atom and with a $(C_1-C_3)$alkanoyl or cyano group; or $R_1$ represents hydrogen; and $R_2$ represents a group $NR_9R_{10}$ in which $R_9$ and $R_{10}$ together with the nitrogen atom to which they are attached constitute a saturated heterocyclic radical of 5 to 11 carbon atoms, which is unsubstituted or substituted once or several times with a $(C_1-C_4)$alkyl; or $R_2$ represents a nonaromatic $C_3-C_{10}$ carbocyclic radical which is unsubstituted or substituted once or several times with a $(C_1-C_4)$alkyl group; or $R_2$ represents a benzyl group which is substituted on the phenyl with one or more identical or different substituents chosen from a halogen atom or a $(C_1-C_4)$alkyl, trifluoromethyl, $(C_1-C_4)$alkoxy or trifluoromethoxy group;

$R_3, R_4, R_5, R_6, R_7, R_8$ each represent independently of each other a hydrogen or halogen atom; and said compound in the form of a base or an addition salt with an acid.

5. The compound of formula (I) as claimed in claim 1, which is chosen from:

4-(4-chlorophenyl)-5-(2,4-dichlorophenyl)-3-methyl-N-piperidin-1-ylthiophene-2-carboxamide;

2-{[4-(4-chlorophenyl)-5-(2,4-dichlorophenyl)-3-methyl-2-thienyl]carbonyl}octahydrocyclopenta[c]pyrrole;

1-(1-{[5-(4-chlorophenyl)-4-(2,4-dichlorophenyl)-2-thienyl]carbonyl}-4-phenylpiperidin-4-yl)ethanone; and 1-(1-{[4-(4-chlorophenyl)-5-(2,4-dichlorophenyl)-2-thienyl]carbonyl }-4-phenylpiperidin-4-yl)ethanone; and said compound in the form of a base or an addition salt with an acid.

6. A method for preparing a compound of formula (I) as claimed in claim 1 comprising:

reacting a compound of formula (II) or a functional derivative thereof:

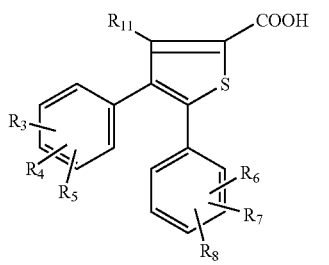

in which $R_3$, $R_4$, $R_5$, $R_6$, $R_7$, $R_8$ and $R_{11}$ are as defined in claim 1, with an amine of formula $HNR_1R_2$ (III) in which $R_1$ and $R_2$ are as defined in claim 1.

7. A pharmaceutical composition comprising at least one compound of formula (I) as claimed in claim 1, in the form of a pharmaceutically acceptable base or salt, in combination with one or more pharmaceutically acceptable excipients.

8. The composition as claimed in claim 7, wherein compound of formula I in which $R_1$ represents hydrogen or a $(C_1-C_4)$alkyl;

$R_2$ represents:

a nonaromatic $C_3-C_{12}$ carbocyclic radical which is unsubstituted or substituted once or several times with a $(C_1-C_4)$alkyl group;

a 1,2,3,4-tetrahydronaphthyl-1 or -2;

a saturated monooxygen- or monosulfur-containing heterocyclic radical of 5 to 7 atoms which is unsubstituted or substituted once or several times with a $(C_1-C_4)$alkyl group;

a saturated mononitrogen-containing heterocyclic radical of 5 to 7 atoms, the nitrogen atom being substituted with a $(C_1-C_4$alkyl, phenyl, benzyl, $(C_1-C_4)$alkoxycarbonyl or $(C_1-C_4)$alkanoyl group;

a $(C_1-C_3)$alkylene group carrying a nonaromatic $C_3-C_{10}$ carbocyclic radical which is unsubstituted or substituted once or several times with a $(C_1-C_4)$alkyl group;

a phenylalkylene group in which the alkylene is $(C_1-C_3)$, which is unsubstituted or substituted on the alkylene with one or more methyl groups, and in which the phenyl is unsubstituted or substituted with one or more identical or different substituents chosen from a halogen atom or a $(C_1-C_4$alkyl, trifluoromethyl, $(C_1-C_4)$alkoxy or trifluoromethoxy group;

a methylene which is substituted with a benzothienyl, benzofuryl, thienyl or furyl radical, said radicals being unsubstituted or substituted with one or more $(C_1-C_4)$ alkyl groups;

an $NR_9R_{10}$ group;

or $R_1$ and $R_2$ together with the nitrogen atom to which they are attached constitute either a piperazin-1-yl or 1,4-diazepan-1-yl radical which is substituted at the 4-position with a phenyl or benzyl group, or a piperidin-1-yl or pyrrolidin-1-yl radical which is mono- or gem-disubstituted with a phenyl, benzyl, $(C_1-C_4)$alkyl, hydroxyl, $(C_1-C_3)$alkanoyl or $(C_1-C_4)$alkoxycarbonylamido group; the phenyl or benzyl groups being unsubstituted or substituted once or several times with a halogen atom and/or a methyl group;

$R_3$, $R_4$, $R_5$, $R_6$, $R_7$, $R_8$ each represent independently of each other a hydrogen or halogen atom, or a $(C_1-C_6)$alkyl, $(C_1-C_6)$alkoxy, trifluoromethyl or $S(O)_n$Alk group;

$R_9$ represents a hydrogen atom or a methyl group;

$R_{10}$ represents a $(C_3-C_6)$alkyl, phenyl or $C_3-C_{10}$ cycloalkyl group, said phenyl and cycloalkyl groups being unsubstituted or substituted with one or more halogen atoms or $(C_1-C_4)$alkyl groups;

or $R_9$ and $R_{10}$ together with the nitrogen atom to which they are attached constitute a saturated or unsaturated heterocyclic radical of 5 to 11 atoms, optionally containing bridged or a spiro carbon and optionally containing a second heteroatom chosen from O or N, said radical being unsubstituted or substituted once or several times with a hydroxyl or phenyl group or a $(C_1-C_4)$alkyl group;

$R_{11}$ represents a hydrogen atom;

n represents 0, 1 or 2;

Alk represents a $(C_1-C_4)$alkyl group; and said compound in the form of a base or an addition salt with an acid.

9. The composition as claimed in claim 7, wherein compound of formula I in which $R_{11}$ represents a $(C_1-C_4)$alkyl or $(C_3-C_7)$cycloalkyl group.

10. The composition as claimed in claim 7, wherein compound of formula (I), in which:

$R_1$ and $R_2$ together with the nitrogen atom to which they are attached constitute a piperidin-1-yl radical which is gem-disubstituted with a benzyl or phenyl group which is unsubstituted or substituted with a halogen atom and with a $(C_1-C_3)$alkanoyl or cyano group; or $R_1$ represents hydrogen; and $R_2$ represents a group $NR_9R_{10}$ in which $R_9$ and $R_{10}$ together with the nitrogen atom to which they are attached constitute a saturated heterocyclic radical of 5 to 11 carbon atoms, which is unsubstituted or substituted once or several times with a $(C_1-C_4)$alkyl; or $R_2$ represents a nonaromatic $C_3-C_{10}$ carbocyclic radical which is unsubstituted or substituted once or several times with a $(C_1-C_4)$alkyl group; or $R_2$ represents a benzyl group which is substituted on the phenyl with one or more identical or different substituents chosen from a halogen atom or a $(C_1-C_4)$alkyl, trifluoromethyl, $(C_1-C_4)$alkoxy or trifluoromethoxy group;

$R_3$, $R_4$, $R_5$, $R_6$, $R_7$, $R_8$ each represent independently of each other a hydrogen or halogen atom; and said compound in the form of a base or an addition salt with an acid.

11. The composition as claimed in claim 7, wherein the compound is chosen from:

4-(4-chlorophenyl)-5-(2,4-dichlorophenyl)-3-methyl-N-piperidin-1-ylthiophene-2-carboxamide;

2-{[4-(4-chlorophenyl)-5-(2,4-dichlorophenyl)-3-methyl-2-thienyl]carbonyl}octahydrocyclopenta[c]pyrrole;

1-(1-{[5-(4-chlorophenyl)-4-(2,4-dichlorophenyl)-2-thienyl]carbonyl}-4-phenylpiperidin-4-yl)ethanone; and 1-(1-{[4-(4-chlorophenyl)-5-(2,4-dichlorophenyl)-2-thienyl]carbonyl}-4-phenylpiperidin-4-yl)ethanone; and said compound in the form of a base or an addition salt with an acid.

12. A method of treatment of a disease in a patient, said disease selected from the group consisting of obesity, inflammation, gastrointestinal disorders, inflammatory phenomena, immune system diseases, psychotic disorders, alcohol dependence and nicotine dependence, comprising administering to said patient a therapeutically effective amount of a compound of formula (I) as claimed in claim 1 in the form of a pharmaceutically acceptable base or salt, optionally, in combination with one more pharmaceutically acceptable excipients.

13. The method as claimed in claim 12, wherein compound of formula I in which

R$_1$ represents hydrogen or a (C$_1$-C$_4$)alkyl;

R$_2$ represents:

a nonaromatic C$_3$-C$_{12}$ carbocyclic radical which is unsubstituted or substituted once or several times with a (C$_1$-C$_4$)alkyl group;

a 1,2,3,4-tetrahydronaphthyl-1 or -2;

a saturated monooxygen- or monosulfur-containing heterocyclic radical of 5 to 7 atoms which is unsubstituted or substituted once or several times with a (C$_1$-C$_4$)alkyl group;

a saturated mononitrogen-containing heterocyclic radical of 5 to 7 atoms, the nitrogen atom being substituted with a (C$_1$-C$_4$)alkyl, phenyl, benzyl, (C$_1$-C$_4$)alkoxycarbonyl or (C$_1$-C$_4$)alkanoyl group;

a (C$_1$-C$_3$)alkylene group carrying a nonaromatic C$_3$-C$_{10}$ carbocyclic radical which is unsubstituted or substituted once or several times with a (C$_1$-C$_4$)alkyl group;

a phenylalkylene group in which the alkylene is (C$_1$-C$_3$), which is unsubstituted or substituted on the alkylene with one or more methyl groups, and in which the phenyl is unsubstituted or substituted with one or more identical or different substituents chosen from a halogen atom or a (C$_1$-C$_4$)alkyl, trifluoromethyl, (C$_1$-C$_4$)alkoxy or trifluoromethoxy group;

a methylene which is substituted with a benzothienyl, benzofuryl, thienyl or furyl radical, said radicals being unsubstituted or substituted with one or more (C$_1$-C$_4$) alkyl groups;

an NR$_9$R$_{10}$ group;

or R$_1$ and R$_2$ together with the nitrogen atom to which they are attached constitute either a piperazin-1-yl or 1,4-diazepan-1-yl radical which is substituted at the 4-position with a phenyl or benzyl group, or a piperidin-1-yl or pyrrolidin-1-yl radical which is mono- or gem-disubstituted with a phenyl, benzyl, (C$_1$-C$_4$)alkyl, hydroxyl, (C$_1$-C$_3$)alkanoyl or (C$_1$-C$_4$)alkoxycarbonylamido group; the phenyl or benzyl groups being unsubstituted or substituted once or several times with a halogen atom and/or a methyl group;

R$_3$, R$_4$, R$_5$, R$_6$, R$_7$, R$_8$ each represent independently of each other a hydrogen or halogen atom, or a (C$_1$-C$_6$)alkyl, (C$_1$-C$_6$)alkoxy, trifluoromethyl or S(O)$_n$Alk group;

R$_9$ represents a hydrogen atom or a methyl group;

R$_{10}$ represents a (C$_3$-C$_6$)alkyl, phenyl or C$_3$-C$_{10}$ cycloalkyl group, said phenyl and cycloalkyl groups being unsubstituted or substituted with one or more halogen atoms or (C$_1$-C$_4$)alkyl groups;

or R$_9$ and R$_{10}$ together with the nitrogen atom to which they are attached constitute a saturated or unsaturated heterocyclic radical of 5 to 11 atoms, optionally containing bridged or a spiro carbon and optionally containing a second heteroatom chosen from O or N, said radical being unsubstituted or substituted once or several times with a hydroxyl or phenyl group or a (C$_1$-C$_4$)alkyl group;

R$_{11}$ represents a hydrogen atom;

n represents 0, 1 or 2;

Alk represents a (C$_1$-C$_4$)alkyl group; and said compound in the form of a base or an addition salt with an acid.

14. The method as claimed in claim 12, wherein compound of formula I in which R$_{11}$ represents a (C$_1$-C$_4$)alkyl or (C$_3$-C$_7$)cycloalkyl group.

15. The method as claimed in claim 12, wherein compound of formula (I), in which:

R$_1$ and R$_2$ together with the nitrogen atom to which they are attached constitute a piperidin-1-yl radical which is gem-disubstituted with a benzyl or phenyl group which is unsubstituted or substituted with a halogen atom and with a (C$_1$-C$_3$)alkanoyl or cyano group;

or

R$_1$ represents hydrogen; and

R$_2$ represents a group NR$_9$R$_{10}$ in which R$_9$ and R$_{10}$ together with the nitrogen atom to which they are attached constitute a saturated heterocyclic radical of 5 to 11 carbon atoms, which is unsubstituted or substituted once or several times with a (C$_1$-C$_4$)alkyl; or R$_2$ represents a nonaromatic C$_3$-C$_{10}$ carbocyclic radical which is unsubstituted or substituted once or several times with a (C$_1$-C$_4$)alkyl group; or R$_2$ represents a benzyl group which is substituted on the phenyl with one or more identical or different substituents chosen from a halogen atom or a (C$_1$-C$_4$)alkyl, trifluoromethyl, (C$_1$-C$_4$)alkoxy or trifluoromethoxy group;

R$_3$, R$_4$, R$_5$, R$_6$, R$_7$, R$_8$ each represent independently of each other a hydrogen or halogen atom; and said compound in the form of a base or an addition salt with an acid.

16. The method as claimed in claim 12, wherein the compound is chosen from:

4-(4-chlorophenyl)-5-(2,4-dichlorophenyl)-3-methyl-N-piperidin-1-ylthiophene-2-carboxamide;

2-{[4-(4-chlorophenyl)-5-(2,4-dichlorophenyl)-3-methyl-2-thienyl]carbonyl}octahydrocyclopenta[c]pyrrole;

1-(1-{[5-(4-chlorophenyl)-4-(2,4-dichlorophenyl)-2-thienyl]carbonyl}-4-phenylpiperidin-4-yl)ethanone; and 1-(1-{[4-(4-chlorophenyl)-5-(2,4-dichlorophenyl)-2-thienyl]carbonyl}-4-phenylpiperidin-4-yl)ethanone; and said compound in the form of a base or an addition salt with an acid.

17. The method as claimed in claim 12, wherein the disease is obesity.

18. The method as claimed in claim 12, wherein the disease is inflammation.

19. The method as claimed in claim 12, wherein the disease is alcohol dependence.

20. The method as claimed in claim 12, wherein the disease is nicotine dependence.

* * * * *